United States Patent [19]

O'Holla

[11] Patent Number: 4,532,926
[45] Date of Patent: Aug. 6, 1985

[54] TWO-PIECE TISSUE FASTENER WITH RATCHET LEG STAPLE AND SEALABLE LATCHING RECEIVER

[75] Inventor: Robert H. O'Holla, Union, N.J.
[73] Assignee: Ethicon, Inc., Somerville, N.J.
[21] Appl. No.: 506,086
[22] Filed: Jun. 20, 1983
[51] Int. Cl.³ .............................................. A61B 17/04
[52] U.S. Cl. ............................ 128/334 C; 227/DIG. 1
[58] Field of Search ........... 128/346, 337, 335, 334 R, 128/334 C, 330, 325, 326, 92 B; 3/1; 227/DIG. 1, 15-18, 77; 411/469, 451, 360, 501, 506, 362-364, 455-457; 24/543, 518, 614, 623, 703, 297, 150 FP, 16 PB, 697, 580, 581, 584, 453, 30.5 P, 537, 515, 513, 503, 94-96

[56] References Cited

U.S. PATENT DOCUMENTS

| Re. 27,391 | 6/1972 | Merser | 24/150 FP X |
|---|---|---|---|
| 306,479 | 10/1884 | Goddard | 24/95 |
| 389,660 | 9/1888 | Mandel et al. | 411/457 X |
| 579,831 | 3/1897 | Ketchum | 24/95 |
| 1,988,233 | 1/1935 | Berendt | 24/95 |
| 2,794,981 | 6/1957 | Brayton | 227/15 |
| 2,881,762 | 4/1959 | Lowrie | 128/337 |
| 2,897,561 | 8/1959 | Megibow | 24/95 |
| 2,900,696 | 8/1959 | Bacon | 24/614 X |
| 3,009,852 | 11/1961 | Gruner | 128/330 X |
| 3,166,072 | 1/1965 | Sullivan | 128/346 X |
| 3,210,820 | 10/1965 | Humiston | 24/584 X |
| 3,326,217 | 6/1967 | Kerr | 227/DIG. 1 C X |
| 3,357,296 | 12/1967 | Lefever | 128/334 C X |
| 3,494,006 | 2/1970 | Brumlik | 411/456 X |
| 3,570,497 | 3/1971 | Lemole | 128/335.5 |
| 3,577,601 | 5/1971 | Mariani et al. | 24/16 |
| 3,683,927 | 8/1972 | Noiles | 128/326 X |
| 3,744,495 | 7/1973 | Johnson | 128/330 |
| 3,802,438 | 4/1974 | Wolvek | 128/335 |
| 3,857,396 | 12/1974 | Hardwick | 128/335 |
| 3,875,648 | 4/1975 | Bone | 227/19 X |
| 3,981,051 | 9/1976 | Brumlik | 411/456 X |
| 4,006,747 | 2/1977 | Kronenthal et al. | 128/337 X |
| 4,038,725 | 8/1977 | Keefe | 24/150 FP |
| 4,060,089 | 11/1977 | Noiles | 128/337 X |
| 4,235,238 | 11/1980 | Ogiu et al. | 128/335 X |
| 4,259,959 | 4/1981 | Walker | 128/337 |
| 4,294,255 | 10/1981 | Geroc | 128/334 C |
| 4,326,531 | 4/1982 | Shimonaka | 128/326 |
| 4,400,833 | 8/1983 | Kurland | 3/1 |
| 4,402,445 | 9/1983 | Green | 128/334 R X |
| 4,454,875 | 6/1984 | Pratt et al. | 128/92 B |

FOREIGN PATENT DOCUMENTS

| 1097171 | 3/1981 | Canada | 128/330 |
|---|---|---|---|
| 1385691 | 12/1964 | France | 40/300 |
| WO83/01190 | 4/1983 | PCT Int'l Appl. | 227/DIG. 1 |
| 82738 | 10/1919 | Switzerland | 128/330 |
| 972731 | 10/1964 | United Kingdom | 128/346 |

Primary Examiner—Michael H. Thaler
Attorney, Agent, or Firm—Robert L. Minier

[57] ABSTRACT

An absorbable fastener is provided to hold together portions of mammalian tissue and includes a T-shaped fastening member and a receiver adapted to receive the leg of the fastening member. The fastening member leg has a plurality of resilient frustoconical members. One of the frustoconical members cooperates with a retaining ring in a bore of the receiver to effect engagement of the fastening member and receiver. The adjacent frustoconical members sealingly engage the receiver and isolate the retaining ring from the body fluids and tissue.

6 Claims, 4 Drawing Figures

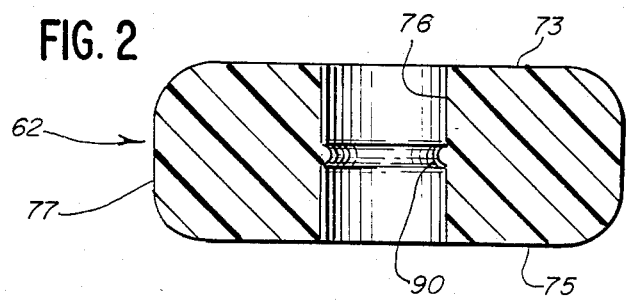
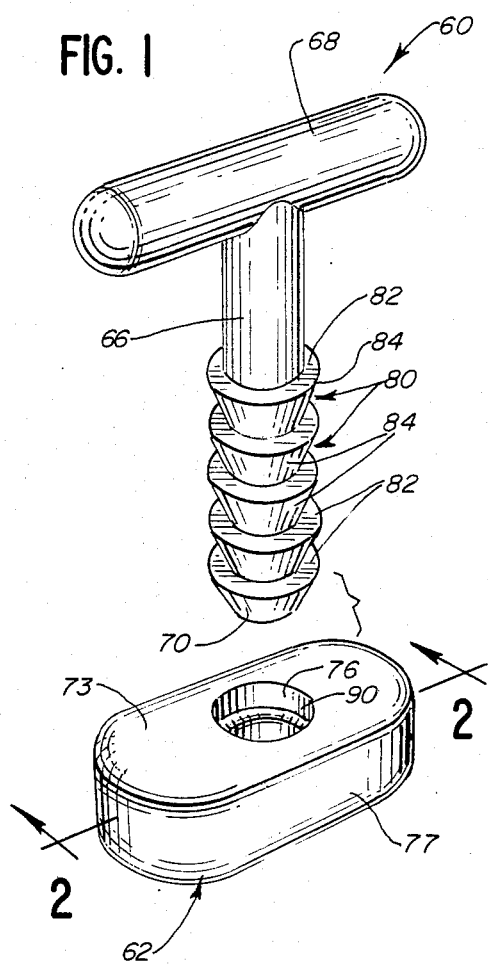
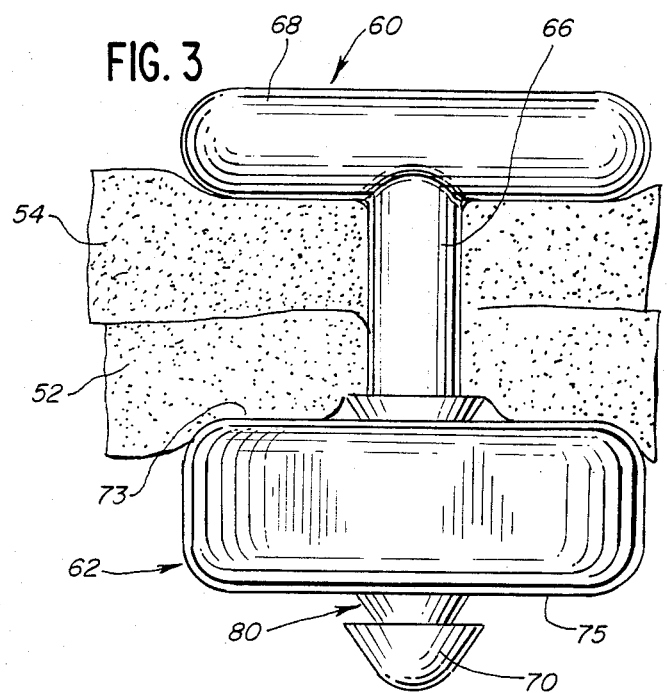
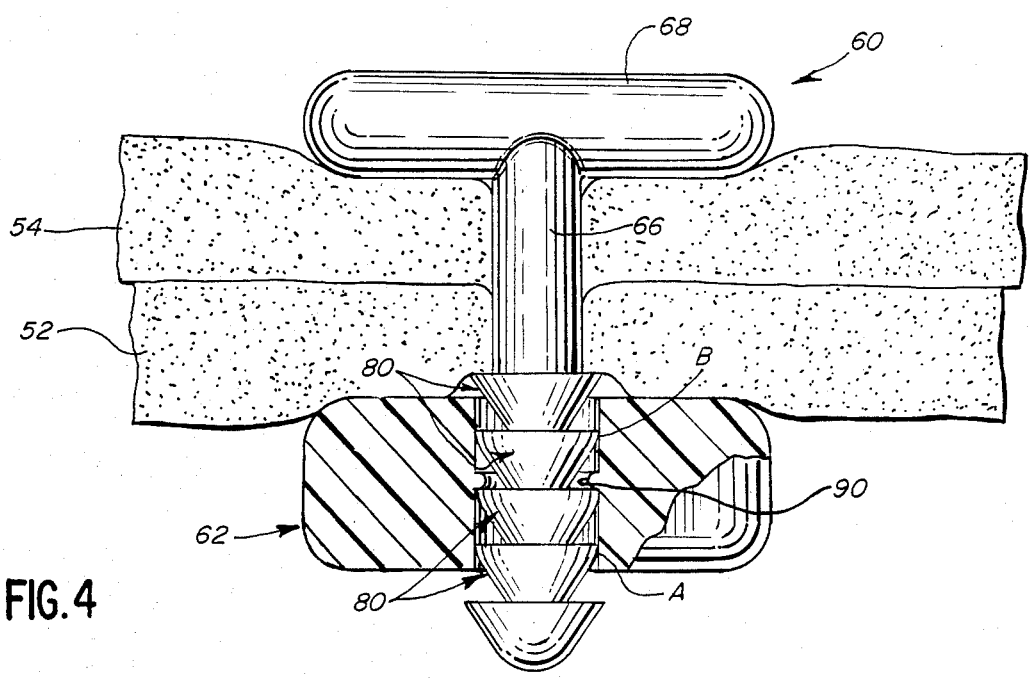

TWO-PIECE TISSUE FASTENER WITH RATCHET LEG STAPLE AND SEALABLE LATCHING RECEIVER

DESCRIPTION

Technical Field

This invention relates, in general, to the fastening together of portions of tissue in surgical procedures.

BACKGROUND OF THE INVENTION

In various surgical procedures, fasteners in the form of staples or the like are employed for holding tissue portions together to facilitate healing of a wound or incision. For example, a locking staple, having a tongue and groove structure by which the staple is locked, is disclosed in U.S. Pat. No. 2,881,762. A metal staple especially adapted for ligating blood vessels is disclosed in U.S. Pat. No. 3,079,608. International patent application No. PCT/SU79/00049 discloses a variety of fastening devices and instruments for performing circular anastomoses on the large intestine. The aforementioned disclosures serve as examples of a wide variety of tissue fastening devices and techniques that may be employed in general and/or specific surgical situations.

One common type of fastening device for joining or holding together soft tissue portions is the generally "U"-shaped staple which is typically fabricated from a suitable metal. Such staples, although generally described as having two legs joined to define a "U"-shape when unclinched, may also be regarded as having a configuration of an "open" loop when unclinched. The legs need not necessarily be parallel but are typically adapted for penetrating the tissue portions and for receiving between them some of the tissue material.

Other examples of U-shaped or open loop staples, as well as of methods and instruments for applying such staples to tissue, are disclosed in U.S. Pat. Nos. 3,252,643, 3,482,428, 3,692,224, 3,790,057, 3,795,034, 3,889,683, 4,198,982, 4,316,468, and 4,319,576.

Other tissue fastening devices have been proposed and differ from staples per se in that these other devices may have a plurality of components and do not have to be clinched in the manner used to set a staple. One such device is disclosed in U.S. Pat. No. 4,060,089 and includes a fastener strip provided with a plurality of longitudinally spaced, parallel prongs which are adapted to penetrate two overlapped tissue portions from one side so that the distal ends of the prongs project from the other side of the tissue portions.

The fastener device further includes a retainer strip which is adapted to be placed on the other side of the tissue portions opposite the fastener strip to engage the ends of the projecting fastener strip prongs and thus secure the tissue portions tightly between the fastener strip and the retainer strip. The retainer strip defines frustoconical openings for receiving the fastener strip prongs which each include a plurality of spaced-apart, frustoconical engaging members for engaging the retainer strip at a desired position relative to the prongs. This provides for the capability of adjusting the distance between the fastener strip and the retainer strip. Such a fastening device may be fabricated from a biodegradable or absorbable material.

Yet another tissue fastening device having a plurality of components is disclosed in co-pending commonly assigned U.S. patent application Ser. No. 349,433, filed Mar. 18, 1982. The fasteners disclosed in that application are made from various polymeric materials and the legs of the U-shaped staple portion of the fastener have a taper to improve the penetration of the staple into tissue.

Although many of the above-discussed types of tissue fastening devices and techniques are satisfactory in various applications, there is a need to provide an improved two-piece fastening device, especially one completely fabricated from absorbable materials.

Also, it would be desirable to provide an improved fastening device fabricated from absorbable materials that can provide primary approximation of the tissue edges to insure that the tissue edges are in continuous contact.

When designing a two-piece fastener fabricated from absorbable materials, care must be taken to ensure that the two-pieces will remain together in clamping relationship on the tissue—even as the fastener material begins to be absorbed by the body. Thus, it wold be desirable to provide an improved two-piece tissue fastener that can be fabricated from absorbable materials and that has a latching mechanism that will remain functional for a sufficiently long time period as the fastener material is being absorbed.

Further, such an improved fastener should provide a desired amount of hemostatic compression to minimize bleeding, but allow some collateral blood circulation to the wound or incision edges of the tissue to promote healing. In addition, such an improved fastener should have the capability to accommodate varying tissue thicknesses and should leave as little tissue cuff or margin as possible in effecting the joining of the tissue.

Further, it would be beneficial if such an improved fastener had a configuration that would enable the fastener to be fabricated with as small a size as possible to minimize dosage. Also, another desirable feature of such an improved fastener would be a fastener configuration that minimizes the possible sites of formation of pockets of infection in the tissue.

Further, such an improved fastener would desirably provide the surgeon with tactile feedback and compensating control during the application of the fastener.

Finally, such an improved fastener should have the capability for maintaining the tissue portions in approximation and compression for a minimum of 21 days in vivo.

It would also be advantageous to provide such a fastener with a design that would facilitate its application to the tissue portions with a simple yet effective method. It would also be desirable if the improved fastener could readily accommodate application by means of an appropriately designed instrument.

SUMMARY OF THE INVENTION

An improved fastener is provided to hold together portions of mammalian tissue, such as are defined by a wound or incision, to facilitate healing of the wound or incision.

The fastener includes a fastening member and a cooperating receiver. The fastening member includes at least one leg with a distal end adapted to be passed through and project from the tissue portions. The fastening member also includes a tissue clamp member connected to the leg and adapted to lie substantially against one of the tissue portions. The leg has on its exterior along at least a portion of its length a plurality of sealing members each defining (1) a resilient, annular sealing portion lying generally in a plane substantially normal to the longitudinal axis of the leg and (2) a surface tapering inwardly from the annular sealing portion towards the distal end of the leg.

A receiver is adapted to be disposed against the other of the tissue portions opposite the fastening member. The receiver defines an aperture therein for receiving the fastening member leg after the leg has been inserted through the tissue portions. The receiver defines an annular retaining ring on the inside surface of the aperture for engaging the annular sealing portion of one of the sealing members of the leg to prevent withdrawal of the leg from the aperture after the leg has been received in the receiver with the sealing portions of adjacent sealing members sealingly engaging the surface of the receiver in the aperture.

To join the tissue portions with the fastener, the two tissue portions are first approximated in a generally face-to-face relationship. Next, the fastening member is positioned on one side of the tissue portions with the leg oriented at an appropriate angle to penetrate the tissue portions. The receiver is positioned on the other side of the tissue portions opposite the fastening member and with the aperture generally in alignment with the fastening member leg.

Relative movement is then effected between the fastening member on the one hand and the tissue portions and receiver on the other hand to cause penetration of the tissue portions by the fastening member leg and to cause a portion of the fastening member leg to be received within the receiver.

The relative movement is effected until the clamp member is disposed against the surface of one of the tissue portions and until the receiver is disposed against the other of the tissue portions. At this point, the retaining ring of the receiver is engaged by one of the annular sealing portions on the fastening member leg and prevents separation of the fastening member and receiver. Adjacent sealing portions on either side of the engaged sealing portion isolate the engaged sealing portion from the body tissue and prevent immediate absorption of the engaged sealing portion.

Numerous other features of various embodiments of a novel tissue fastener will be apparent from the following detailed description and accompanying drawings.

BRIEF DESCRIPTION OF THE DRAWINGS

In the accompanying drawings forming part of the specification, and in which like numerals are employed to desginate like parts throughout the same.

FIG. 1 is a perspective view of a first embodiment of the fastener of the present invention which includes a fastening member and receiver;

FIG. 2 is a cross-sectional view taken generally along the plane 2—2 in FIG. 1;

FIG. 3 is a fragmentary, partial cross-sectional view of two portions of mammalian tissue defined by an incision or wound with some of the tissue cut away to better show interior detail and illustrating the fastening member of FIG. 1 inserted through the two portions of the tissue and fully engaged with the receiver of FIG. 1; and FIG. 4 is a view similar to FIG. 3 but showing a portion of the receiver cut away to illustrate the latching mechanism.

DESCRIPTION OF THE PREFERRED EMBODIMENT

This invention may be used in many different forms. The specification and accompanying drawings disclose only one specific form as an example of the use of the invention. The precise shapes and sizes of the components herein described are not essential to the invention unless otherwise indicated. The invention is not intended to be limited to the embodiment illustrated, and the scope of the invention will be pointed out in the appended claims.

A preferred embodiment of the fastener is illustrated in FIGS. 1-4 and is designated generally therein by reference numeral 50. The fastener 50 is illustrated in FIGS. 3 and 4 in the fully assembled, "set" configuration wherein it is shown holding together two portions 52 and 54 of mammalian tissue, such as are defined by a wound or incision, to facilitate healing of the wound or incision. Typically, a plurality of such fasteners 50 would be used to close a wound or incision. However, with just a small wound or incision, one fastener 50 may be sufficient.

The fastener 50 includes two components, a generally T-shaped fastening member 60 and a receiver 62, which are initially separated as illustrated in FIG. 1 and which are adapted to cooperate to compress or hold between them the tissue portions.

The fastening member includes at least one leg 66 which is adapted to be passed through and project from the tissue portions. The leg 66 has a distal end 70 which is preferably rounded to aid in its passing through the tissue portions and through the receiver 62 in a manner described in detail hereinafter.

Connected to the other end of the leg 66 is a outwardly projecting cross piece or enlarged member, such as clamp member 68. The clamp member 68 and leg 66 are oriented relative to each other in a generally perpendicular relationship to define a generally T-shaped configuration. The cross member or clamp member 68 may have the shape of a regular parallelpiped (as illustrated) or may have any other suitable shape.

Preferably, the leg 66 has a generally solid, cylindrical shape. The leg 66 has on its exterior along at least a portion of its length a plurality of sealing members 80. Preferably, each sealing member 80 has a frustoconical shape. Each sealing member 80 defines (1) a resilient, annular sealing portion 82 lying generally in a plane substantially normal to the longitudinal axis of the leg 66 and (2) a surface 84 (such as the frustoconical surface illustrated) tapering inwardly from the annular sealing portion 82 towards the distal end 70 of the leg 66. As can be seen in FIG. 1, the surface 84 faces away from the clamp member 68.

As best illustrated in FIG. 3, the receiver 62 is adapted to be disposed against one of the tissue portions opposite the fastening member 60. The receiver 62 defines a first side 73 (FIG. 1) adapted to be disposed against a tissue portion (tissure portion 52 shown in FIGS. 3 and 4). The receiver 62 also has a second side 75 (FIG. 2) facing generally away from the first side 73. An exterior, peripheral surface 77 extends between the first and second sides of the receiver 62.

The receiver 62 defines an aperture, such as a generally cylindrical bore 76 (FIGS. 1 and 2), extending from the first side 73 of the receiver to the second side 75 of the receiver. The bore 76 has a diameter less than the largest diameter of the annular sealing portion 82 of each sealing member 80. However, the diameter of the bore 76 is greater than the smallest cross sectional dimension of the portions of the fastening member leg between the annular sealing portions 82. In the embodiment illustrated, the bore 76 has a length or depth sufficient to accommodate (i.e., surround) a length of the fastening member leg having at least four of the sealing members 80.

The receiver 62 also defines an annular retaining or latching ring 90 on the inside surface of the aperture or bore 76 for engaging an annular sealing portion 82 of one of the sealing members 80. This prevents withdrawal of the fastening member leg 66 from the bore 76 after the leg 66 has been received in the receiver 62 with the sealing portions 82 of adjacent sealing members 80 sealingly engaging the surface of the receiver 62 in the bore 76.

Preferably, the latching or retaining ring 90 is integrally formed with the receiver 62. The ring 90 projects inwardly into the bore 76 an amount sufficient to prevent movement of a fastening member sealing portion 82 past the ring 90 when the fastening member 60 is pulled relative to the receiver 62 in a direction tending to separate the fastening member 60 and receiver 62. However, the retaining ring 90 does not project so far inwardly that movement of the sealing members 80 past the retaining ring 90 in the other direction is prevented.

The fastening member 60 and receiver 62 may be formed from suitable materials, such as thermoplastic polymer materials that are absorbable by mammalian tissue. For example, the fastening member and receiver may be molded from absorbable polymers or copolymers of poly-dioxanone, lactide, glycolide and the like. The fastener may also be molded from a combination of both such materials.

The fastener 50 is used to join the tissue portions 52 and 54 (FIGS. 2 and 3) in a novel manner. Specifically, the tissue portions 52 and 54 are first approximated in surface-to-surface relationship as best illustrated in FIG. 2. Then the fastening member 60 is positioned on one side of the tissue portions with the leg 66 oriented at an appropriate angle to penetrate the tissue portions. The receiver 62 is held on the other side of the tissue portions opposite the fastening member 60 with the bore 76 generally in alignment with the fastening member leg 66.

Next, relative movement between the fastening member 60 and the receiver 62 is effected to urge the fastening member and the receiver closer together to cause the fastening member leg 66 to penetrate the tissue portions 52 and 54 and to locate at least a portion of the fastening member leg 66 within the receiver 62. The relative movement between the fastening member 60 and the receiver 62 is terminated when the clamp member 68 is at a desired distance from the receiver 62 to secure the tissue portions together. Preferably, this movement is terminated after the tissue portions have been compressed together a desired amount.

As the fastening member leg 66 is pushed through receiver 62, the sealing members 80 are inwardly deformed as they pass through the smaller diameter bore 76 and as they are moved past the even smaller diameter retaining ring 90. When a member 80 has passed the retaining ring 90, the member 80 expands outwardly into contact with the wall of the bore 76.

When the tissue portions 54 and 52 have been compressed the desired amount, the applied forces effecting the relative movement between the fastening member 60 and the receiver 62 are removed. Then the fastening member 60 and the receiver 62 tend to be forced apart by the compressed tissues. This may effect a small, reverse relative movement. However, this small, reverse movement is limited as will next be explained.

When the relative positions of the fastening member 60 and receiver 62 are as illustrated in FIGS. 3 and 4, a sealing member 80 immediately adjacent, but below, the receiver retaining ring 90 will limit any reverse relative movement between the fastening member 60 and receiver 62. In this orientation, the retaining ring 90 in the bore 76 of the receiver 62 engages the annular sealing portion 82 of the member 80 and prevents withdrawal of the leg 66 from the receiver 62.

The distal end of the fastening member leg 66 will typically protrude from the receiver 62 opposite the side of the receiver 62 that is contacting one of the tissue portions. If desired, the protruding end of the leg 66 may be severed flush with the bottom of the receiver 62 by a suitable means. Preferably, during the step of severing the protruding portion of the fastening member leg 66, the protruding portion of the fastening member leg is surrounded with a suitable container for catching the leg protruding portion after it is severed so as to prevent the severed portion of the leg from falling into the surrounding tissue or body cavity.

Regardless of whether the projecting leg portion of the fastening member 60 is severed flush with the bottom of the receiver 62, it is seen that the sealing members 80 within the bore 76 of the receiver 62 sealingly engage the sides of the bore 76 and isolate the retaining ring 90. Specifically, with reference to FIG. 4, it is seen that the third member 80 from the bottom of the leg 66 is engaged with, and retained by, the retaining ring 90. The adjacent, second member 80 from the bottom of the leg (below the member 80 engaged with the ring 90) is sealingly engaged with the bore 76 in region A. Similarly, the member 80 immediately adjacent and above the member 80 engaged with the ring 90 is also sealingly engaged with the bore 76 at region B.

The sealing engagement effected between the sealing members 80 and the receiver 62 at regions A and B effectively prevents the ingress of body fluids and tissue. Thus, the relatively small amount of material forming the latching ring 90 and the annular sealing portion 82 is not immediately affected by the body fluids and tissues and is not immediately absorbed. Hence, the novel retaining or latching structure is initially undisturbed and remains functional.

On the other hand, the exterior portions of the fastening member 60 and of the receiver 62 are in direct contact with the body fluids and tissues. Absorption of these exterior portions begins immediately. By the time the fastener material is absorbed exterior of the seal regions A and B, the clamped tissues portions 52 and 54 have healed sufficiently and further clamping is no longer required. Thus, ingress of the body fluids and tissues to the region of the retaining ring 90 can be permitted, and indeed does occur. Complete absorption of the retaining ring 90 and other interior portions of the fastener 50 can then occur.

The above-described method for applying the fastener 50 to the tissue portions 52 and 54 may be effected with a suitable instrument specifically designed for holding the fastening member 60 and receiver 62 and for driving the fastening member 60 through the tissue portions and into engagement with the receiver 62.

Such an instrument (not illustrated) may include a pair of pivotally mounted jaws with one of the jaws adapted for holding the receiver 62 on one side of the tissue portions and with the other of the jaws adapted for holding the fastening member 60 on the other side of the tissue portions. A suitable driving member may be provided as part of the instrument for driving the fastening member 60 from its holding jaw, into the tissue portions, and finally into engagement with the receiver 62. To facilitate tissue penetration, the fastening member leg distal end 70 could, if desired, be made more pointed than is illustrated.

The instrument may include a suitable mechanism for severing the protruding portion of the fastening member leg 66 after the fastening member 60 and receiver 62 have been locked together with the tissue portions under the desired amount of compression. It is to be realized that such an instrument might be preferably provided with means for applying a plurality of such fasteners simultaneously.

From the foregoing, it will be observed that numerous variations and modifications may be effected without departing from the true spirt and scope of the novel concept of the invention. It is to be understood that no limitation with respect to the specific article, instrument, and methods illustrated herein is intended or should be inferred. It is, of course, intended to cover by the appended claims all such modifications as fall within the scope of the claims.

What is claimed is:

1. A fastener adapted to hold together two portions of mammalian tissue, such as are defined by a wound or incision, to facilitate healing of the wound or incision, said fastener being made from an absorbable polymer, said fastener comprising:
   a fastening member including at least one leg with a distal end adapted to be passed through and project from said tissue portions, said fastening member also including a tissue clamp member connected to said leg and adapted to lie substantially against one of said tissue portions, said leg having on its exterior along at least a portion of its length a plurality of sealing members each defining (1) a resilient, annular sealing portion lying generally in a plane substantially normal to the longitudinal axis of said leg and (2) a surface tapering inwardly from said annular sealing portion towards the distal end of said leg; and
   a receiver adapted to be disposed against the other of said tissue portions opposite said fastening member, said receiver defining an aperture therein for receiving and fastening member leg after said leg has been inserted through said tissue portions, said receiver defining an annular retaining ring on the inside surface of said aperture for engaging said annular sealing portion of one of said sealing members of said leg to prevent withdrawl of said leg from said aperture after said leg has been received in said receiver with the sealing portions of adjacent sealing members sealingly engaging the surface of said receiver in said aperture, whereby said annular retaining ring is isolated from the mammalian tissue by the sealing portions to prevent immediate absorption of said ring.

2. The fastener in accordance with claim 1 in which said fastening member is a generally T-shaped member, in which a portion of said leg has a generally solid cylindrical shape, and in which the distal end of said leg opposite said clamp member has a generally rounded configuration to facilitate placement of said leg through said tissue.

3. The fastener in accordance with claim 1 in which said leg is generally perpendicular to said clamp member.

4. The fastener in accordance with claim 1 in which said fastening member is molded from an absorbable thermoplastic polymer and in which said receiver is molded from an absorbable thermoplastic polymer.

5. The fastener in accordance with claim 1 in which each said receiver has (1) a first side adapted to be disposed against the other of said tissue portions, (2) a second side facing generally away from said first side, and (3) an exterior peripheral surface extending between said first and second sides;
   in which said receiver aperture extends from said first side of said receiving member to said second side of said receiver; and
   in which each said receiver aperture is a bore having a diameter less than the largest diameter of said sealing member annular sealing portion of said fastening member and in which said receiver bore has a depth sufficient to accommodate a length of said fastening member leg having at least four of said sealing members.

6. A fastener adapted to hold together two portions of mammalian tissue, such as are defined by a wound or incision, to facilitate healing of the wound or incision, said fastener being made from an absorbable polymer, said fastener comprising:
   a generally T-shaped fastening member, said fastening member comprising a leg adapted to be passed through and project from said tissue portions and comprising a tissue clamp member connected to one end of said leg and adapted to lie substantially against one of said tissue portions; said leg having on its exterior along at least a portion of its length a plurality of substantially frustoconical members each defining (1) a resilient, annular sealing portion lying generally in a plane substantially normal to the longitudinal axis of said leg and (2) a frustoconical surface tapering inwardly from said annular sealing portion and facing away from said clamp member; and
   a receiver having a first side adapted to be disposed against the other of said tissue portions and a second side facing generally away from said first side; said receiver having an exterior peripheral surface extending between said first and second sides; said receiver defining a bore extending from said first side of said receiver to said second side of said receiver for receiving said fastening member leg after said leg has been inserted through said tissue portions, said receiver defining an annular retaining ring on the inside surface of said bore for engaging said annular sealing portion of one of said frustoconical members of said leg to prevent withdrawal of said leg from said bore after said leg has been received in said receiver with the sealing portions of adjacent frustoconical members sealingly engaging the surface of said receiver in said bore, whereby said annular retaining ring is isolated from the mammalian tissue by the sealing portions to prevent immediate absorption of said ring.

* * * * *